(12) United States Patent
Hussein (10) Patent No.: US 10,765,358 B2
(45) Date of Patent: Sep. 8, 2020

(54) DENTAL INSTRUMENT FOR MEASURING A DEGREE OF TAPERING OF A SIDE WALL OF A TOOTH

(71) Applicant: University of Florida Research Foundation, Inc., Gainesville, FL (US)

(72) Inventor: Hind Sattar Hussein, Lakewood Ranch, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 113 days.

(21) Appl. No.: 16/152,690

(22) Filed: Oct. 5, 2018

(65) Prior Publication Data

US 2019/0104983 A1   Apr. 11, 2019

Related U.S. Application Data

(60) Provisional application No. 62/570,829, filed on Oct. 11, 2017.

(51) Int. Cl.
| | |
|---|---|
| *A61B 5/00* | (2006.01) |
| *A61C 19/04* | (2006.01) |
| *G09B 19/24* | (2006.01) |
| *A61B 5/107* | (2006.01) |
| *G09B 23/28* | (2006.01) |

(52) U.S. Cl.
CPC .......... *A61B 5/4547* (2013.01); *A61B 5/1071* (2013.01); *A61C 19/04* (2013.01); *G09B 19/24* (2013.01); *G09B 23/283* (2013.01); *A61C 2201/002* (2013.01)

(58) Field of Classification Search
CPC ......... A61C 19/04; A61C 3/00; A61B 5/4547; A61B 5/1071
See application file for complete search history.

(56) References Cited

U.S. PATENT DOCUMENTS

| | | | | |
|---|---|---|---|---|
| 5,882,195 A | * | 3/1999 | Low .................. | A61B 1/247 433/140 |
| 2005/0255421 A1 | * | 11/2005 | Michaelson ....... | A61C 3/10 433/4 |
| 2006/0029906 A1 | * | 2/2006 | Hill .................... | A61C 3/00 433/141 |
| 2015/0348320 A1 | * | 12/2015 | Pesach .............. | A61C 9/0053 382/128 |
| 2017/0319298 A1 | * | 11/2017 | Lee .................... | A61C 8/0089 |

* cited by examiner

*Primary Examiner* — Nicholas D Lucchesi
(74) *Attorney, Agent, or Firm* — Thomas Horstemeyer, LLP (57) ABSTRACT

A dental instrument configured to measure a degree of tapering of a side wall of a tooth is described. The dental instrument may include a handle and a taper measuring component coupled to a distal end of the handle. The taper measuring component includes a first, second, and third elongated member. A bottom surface may be formed at a coupling point of the second and third elongated member, where the second elongated member is configured to be substantially vertical when the bottom surface is placed adjacent to a tooth, and the third elongated member projecting radially from the second elongated member at a predefined angle. The third elongated member is shaped and positioned to rest substantially flush along the at least one side wall of the tooth when a degree of tapering of the tooth is substantially similar to the angle, and may include a measuring component.

17 Claims, 6 Drawing Sheets

DENTAL INSTRUMENT FOR MEASURING A DEGREE OF TAPERING OF A SIDE WALL OF A TOOTH

CROSS-REFERENCE TO RELATED APPLICATION

This application claims the benefit of and priority to U.S. Provisional Patent Application No. 62/570,829 entitled "DENTAL INSTRUMENT FOR MEASURING A DEGREE OF TAPERING OF A SIDE WALL OF A TOOTH," filed Oct. 11, 2017, the contents of which being incorporated by reference in their entirety herein.

BACKGROUND

Tooth measurement and crown preparation is a common procedure in general dental practice and dental students are often required to demonstrate competency in this procedure to graduate from dental school. The training of these techniques is subjective, as a dentist or student relies upon an "eyeballing" of a crown preparation rather than relying upon a definitive measure. Moreover, dental students are required to pass taper criteria in the Manikin-based dental examination for crown preparation, as the dental students are required to taper a tooth wall from nearly parallel to 12°. The dental student can be subject to a failing grade if the taper of the tooth wall is grossly over-reduced, or reduced to over 16°. Students and exam administrators do not have an objective tool to measure a degree of the tapering of the side wall of a tooth, often meaning that dental students are subject to a passing or failing score based on a subjective opinion of the instructor. As such, a need exists to perform a more formal assessment of a tapering of a side wall of a tooth.

SUMMARY OF THE INVENTION

Various embodiments for a dental instrument configured to measure a degree of tapering of a side wall of a tooth are described. The dental instrument may include a handle and a taper measuring component coupled to a distal end of the handle. The tape measuring component may include a first elongated member, a second elongated member, and a third elongated member in some embodiments. The taper measuring component includes a bottom surface formed at a coupling point of the second elongated member and the third elongated member, where the second elongated member is configured to be substantially vertical when the bottom surface of the taper measuring component is placed adjacent to the tooth such that the second elongated member is substantially parallel to a vertical (or longitudinal) axis of the tooth. The third elongated member may project radially from the second elongated member at a predefined angle. The third elongated member is shaped and positioned to rest substantially flush along the at least one side wall of the tooth in response to a degree of tapering of the tooth being substantially similar to the predefined angle.

Moreover, a method for measuring a degree of tapering of a side wall of a tooth is provided. The method may include, for example, providing a dental instrument adapted to measure the degree of tapering of the side wall of a prepared tooth, where the dental instrument includes a handle and a taper measuring component. The taper measuring component may include, for instance, a first elongated member, a second elongated member, and a third elongated member. A bottom surface may be formed at a coupling point of the second elongated member and the third elongated member. The second elongated member may be configured to be substantially vertical when the bottom surface of the taper measuring component is placed adjacent to the tooth. The third elongated member may project radially from the second elongated member at a predefined angle. The method may further include positioning the taper measuring component adjacent to the tooth using the handle and measuring the degree of tapering of the side wall of the tooth based at least in part on whether the second elongated member rests substantially flush along the side wall of the prepared tooth.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
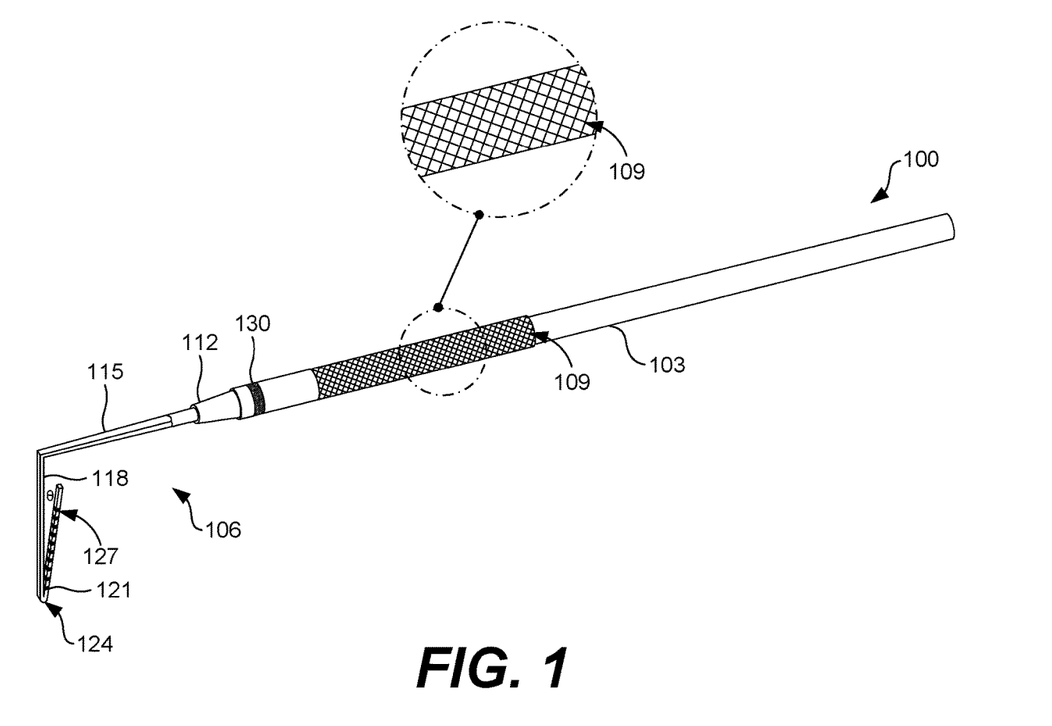
FIG. 1 is a perspective view of a dental instrument configured to measure a degree of tapering of a side wall of a tooth according to various embodiments of the present disclosure.
Figure 2:
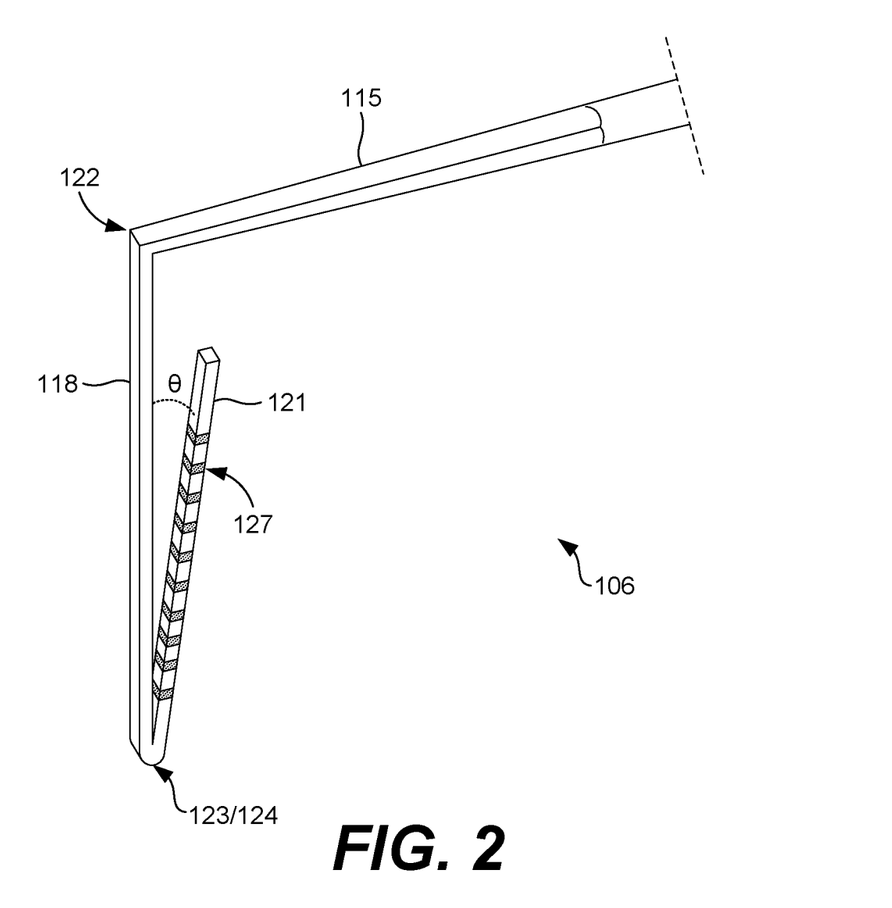
FIG. 2 is an enhanced perspective view of a taper measuring component, or a tip of a dental instrument, configured to measure a degree of tapering of a side wall of a tooth is shown according to various embodiments of the present disclosure.

The present disclosure relates to a dental instrument configured to measure a degree of tapering of a side wall of a tooth. Referring now to FIGS. 1 and 2, a dental instrument 100 configured to measure a degree of tapering of a side wall of a tooth is shown according to various embodiments. The dental instrument 100 may include, for example, a handle 103 and a taper measuring component 106 coupled to a distal end of the handle 103. The handle 103 may include metal, plastic, or other suitable material, and may include a textured grip 109 that facilitates holding the handle 103. In some embodiments, the handle 103 may include a universal tool handle known in the dental field, where the taper measuring component 106 may be detachably attached to the handle 103 by way of a coupler 112 in some embodiments.

In various embodiments, the coupler 112 may be conical (or "cone-shaped") and may include a threaded aperture (not shown) that allows a threaded portion (not shown) of a coupling member 115 of the taper measuring component 106 to be rotated or screwed into the threaded aperture of the coupler 112. In other embodiments, the taper measuring component 106 may be detachably attached to the handle 103 through various other coupling connections, as may be appreciated. Further, in alternative embodiments, the taper measuring component 106 may be coupled to the handle in a fixed (and non-removable) state relative to the handle 103.

By placement of the taper measuring component 106 adjacent to and/or parallel to a tooth, and by virtue of the shape and positioning of the various components thereof, the dental instrument 100 is configured to measure the degree of tapering of a side wall of the tooth, as will be discussed. As noted above, the taper measuring component 106 may include the coupling member 115 configured to detachably or permanently attach the taper measuring component 106 to the handle 103 at a straight (180 degree) angle, or at another angle suitable for placement adjacent to a tooth. The coupling member 115 may also be referred to as a first elongated member, which extends from and substantially parallel to a body of the handle 103. Further, the taper measuring component 106 may include a second elongated member 118 coupled to a third elongated member 121. The second elongated member 118 may form a 90 degree angle, or other appropriate angle, with the first elongated member (i.e., the coupling member 115).

Referring specifically to FIG. 2, an enhanced view of the taper measuring component 106 is shown. The taper measuring component 106 may include, for example, a first bend 122 and a second bend 123 which may form or otherwise define the first elongated member 115, the second elongated member 118, and the third elongated member 121 from, for instance, a single piece of metal, plastic, or other suitable material. As may be appreciated, the first bend 122 may be described as defining the first elongated member 115 and the second elongated member 118, whereas the second bend 123 may define the second elongated member 118 and the third elongated member 121.

In some embodiments, the second elongated member 118 may be sized and positioned to be substantially vertical or substantially parallel to a vertical axis of a tooth when a bottom surface 124, or the second bend 123, of the taper measuring component 106 is placed on the finishing line of a tooth preparation or parallel to the tooth, as will be discussed. In some embodiments, the width of the bottom surface 124 may be less than 0.5 mm or as small as possible without forming a substantially sharp tip. The third elongated member 121 may be configured to project radially from the second elongated member 118 at a predefined angle (θ). In some embodiments, the third elongated member 121 may be shaped and positioned to rest substantially flush along the side wall of the prepared tooth in response to a degree of tapering of the tooth being substantially similar to the predefined angle (θ). A substantially similar angle may include one that is ±4 degrees for example. The second elongated member 118 and/or the third elongated member 121 may have a length of approximately 12 mm to approximately 15 mm in some embodiments, although other suitable lengths may be employed.

Further, in various embodiments, the third elongated member 121 may include a measuring component 127 with a calibration starting from the bottom surface 124 (e.g., having metrics increasing upwards from the bottom surface 124). The measuring component 127 may include marks and/or metrics spaced consistent and predetermined distances from one another that facilitate measuring a height of a tooth or tooth wall. To this end, both the tapering of the tooth and the height of the tooth may be measured in a single task using the dental instrument 100.

By virtue of the angles formed in the first bend 122 and the second bend 123, the taper measuring component 106 may be substantially triangular shaped, as shown in FIGS. 1 and 2. While the third elongated member 121 is shown as not being connected to a bottom of the coupling member 115, in other embodiments, the third elongated member 121 may have a length such that a distal end of the third elongated member 121 couples to a bottom of the coupling member 115. The coupling member 115, the second elongated member 118, and the third elongated member 121 of the taper measuring component 106 may be formed from a single part, such as a single piece of metal, plastic, or other suitable material that may be bended, shaped, or otherwise formed to have a rigid shape and positioned suited for measuring a taper of a tooth wall. In some embodiments, the cross-section of the taper measuring component 106 may be square, rectangular, circular, ovular, or other suitable shape.

Even further, in some embodiments, the handle 103 of the instrument may include an indicator 130, such as a label or a color-coded band, that is indicative of the predefined angle (θ). For instance, the indicator 130 may include a white band for a dental instrument 100 having a predefined angle of eight degrees, a black band for a dental instrument 100 having a predefined angle of twelve degrees, a red band for a dental instrument 100 having a predefined angle of sixteen degrees, and so forth. Additionally, the indicator 130 may use other color coding ideal for the instrument to be easily and quickly identified due to the visual color of the indicator 103.

Figure 3:
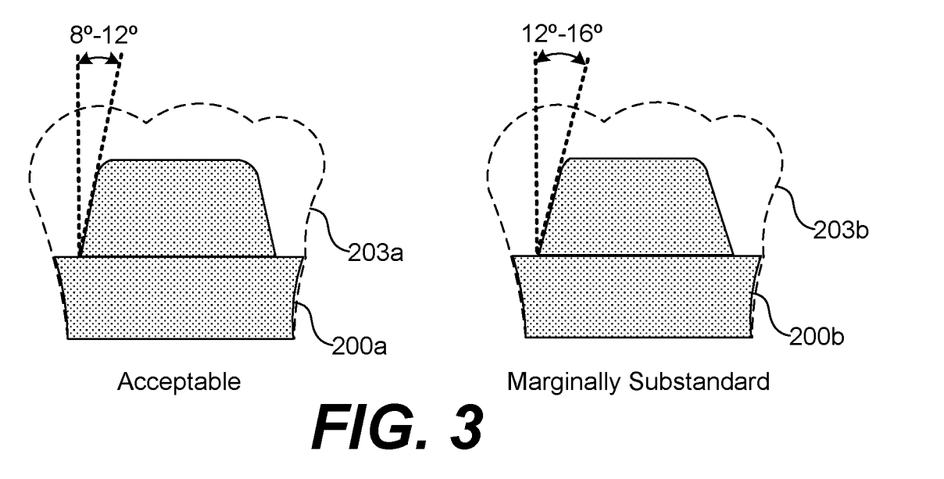
FIG. 3 is a drawing illustrating acceptable and marginally substandard tapers of a side wall of a tooth according to various embodiments of the present disclosure.

Turning now to FIG. 3, an example of a tooth 200a having an acceptable degree of tapering (e.g., eight degrees to twelve degrees) and an example of a tooth 200b having a marginally substandard degree of tapering (e.g., twelve degrees to sixteen degrees) is shown. For instance, a dentist or a dental student may be required to modify a shape of a tooth 200 for its original tooth shape 203a . . . 203b, also referred to as a dental crown, on the tooth 200. In the Manikin-based dental examination for crown preparation, dental students are required to taper a tooth wall from nearly parallel to 12°. The dental student can be subject to a failing grade if the taper of the tooth wall is grossly over-reduced, or reduced to over 16°.

Figure 4:
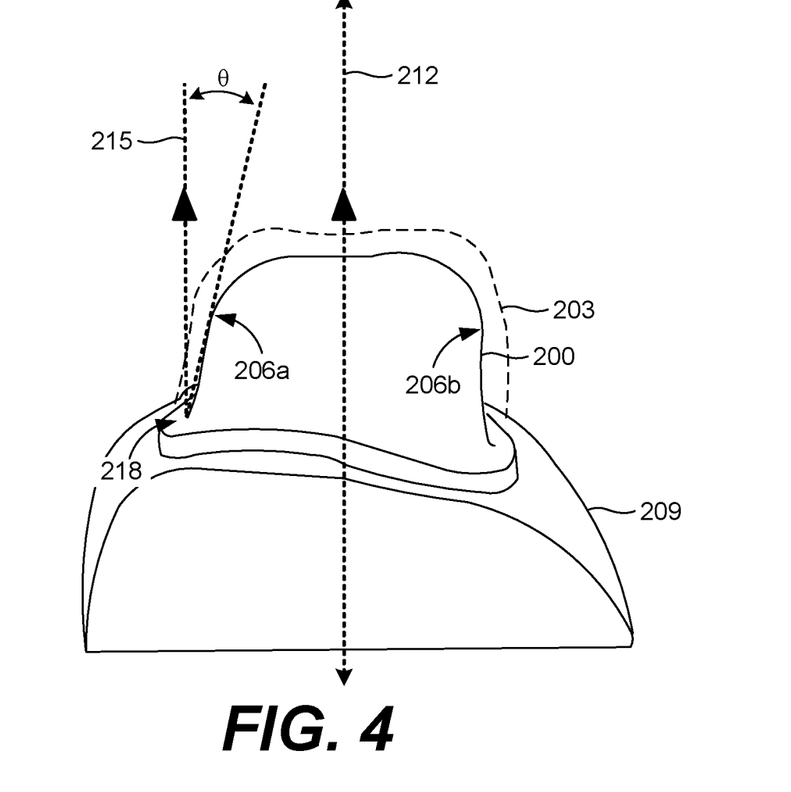
FIG. 4 is a perspective view of a tooth illustrating a degree of taper of a side wall of the tooth according to various embodiments of the present disclosure.
Figure 5:
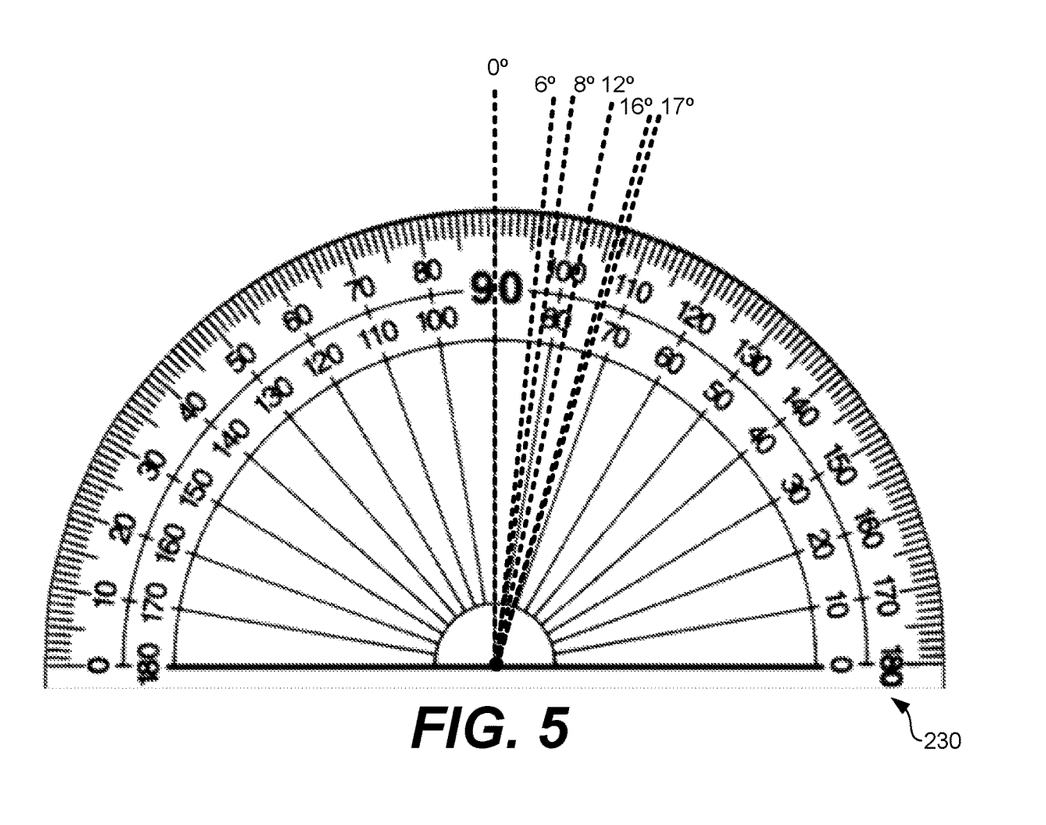
FIG. 5 is a drawing illustrating various degrees ideal for measuring a taper of a side wall of at tooth according to various embodiments of the present disclosure.

Moving on to FIG. 4, a model of a tooth 200 is shown. The tooth 200 may include a pair of side walls 206a . . . 206b, as may be appreciated, that must be tapered from its original tooth shape 203 to the tooth 200 shown in FIG. 4. Gums 209 are also shown. The tapering, or the degree of tapering, is measured as an angle between an axis 215 substantially parallel to a vertical axis 212 of the tooth 200 and a side wall 206 of the tooth 200, denoted in FIG. 3 as theta (θ). FIG. 5 illustrates common tapering angles shown on a protector diagram 230 that can be measured using the dental instrument 100, such as six degrees, eight degrees, twelve degrees, sixteen degrees, seventeen degrees, etc. The training of tapering techniques is often subjective. For instance, dentists, dental students, and other dental practitioners rely upon an "eyeballing" of a crown preparation rather than relying upon a definitive measure.

Figure 6:
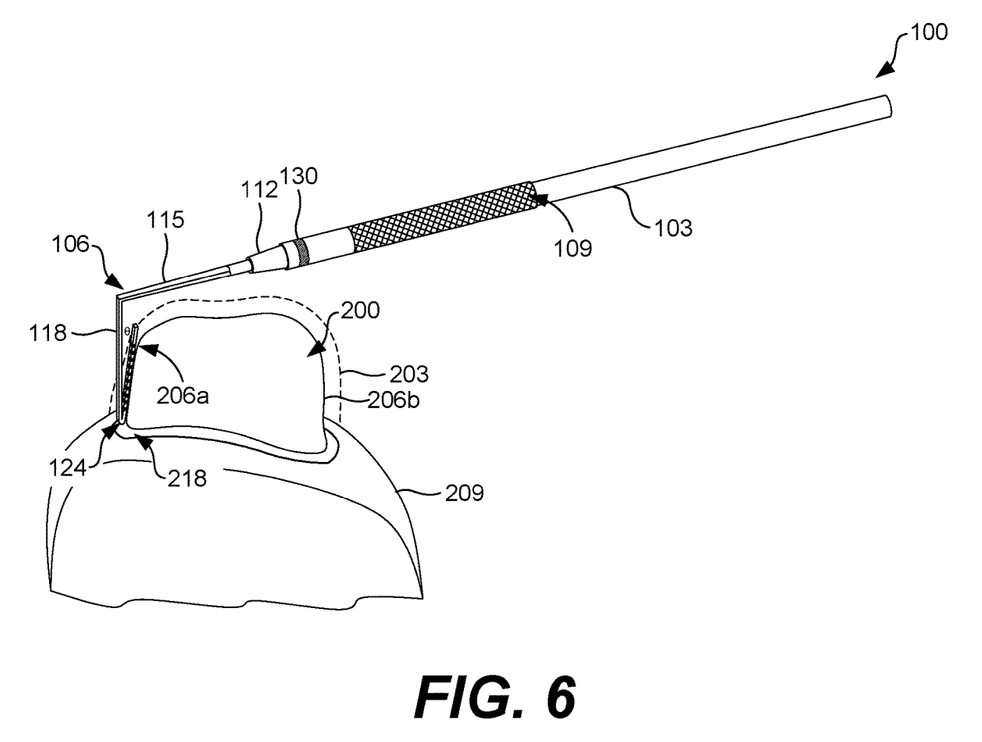
FIG. 6 is a perspective view of the dental instrument measuring a degree of tapering of a side wall of a tooth according to various embodiments of the present disclosure.

Moving on to FIG. 6, an example placement of the dental instrument 100 relative to a tooth 200 is shown according to various embodiments. For instance, the bottom surface 124 of the taper measuring component 106 may be placed on or near the gums 209 adjacent to a tooth 200 or, in other words, on the finishing line 218 of a tooth preparation, such that the second elongated member 118 is substantially parallel to a vertical axis 212 of the tooth. The degree of tapering of the side wall 206 of the tooth 200 based at least in part on whether the third elongated member 121 rests substantially flush with a surface of the side wall 206 of the tooth 200. For instance, if the third elongated member 121 does not rest substantially flush with a surface of the side wall 206 of the tooth 200, another instrument having a different predefined angle (θ) may be used, or a better eyeball test may be applied based on how closing the tapering of the side wall 206 of the tooth 200 conforms to the predefined angle (θ) of the taper measuring component 106. Alternatively, if the third elongated member 121 rests substantially flush along the side wall 206 of the tooth 200, it may be assumed that the tapering of the side wall 206 of the tooth 200 is equal or substantially similar to the predefined angle (θ) of the taper measuring component 106.

To this end, the dental instrument 100 may be used to measure a degree of tapering of a side wall 206 of a tooth 200 when practicing crown preparation or when performing a crown preparation during a dental exam on a model tooth. Alternatively, the dental instrument may be used in actual practice by a dentist, dental assistant, or other dental practitioner on a mammalian tooth.

Figure 7:
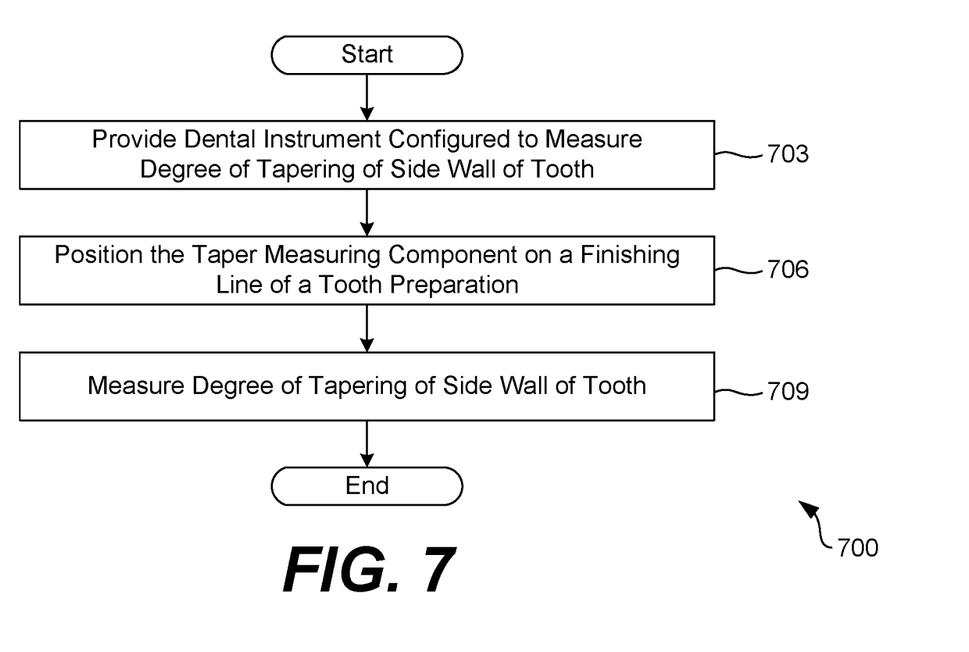
FIG. 7 is a flowchart describing an example use of the dental tool of FIG. 1 according to various embodiments of the present disclosure.

Referring next to FIG. 7, shown is a flowchart 700 that provides an example of operation or use of the dental instrument 100 according to various embodiments. It is understood that the flowchart of FIG. 7 provides merely an example of the many different types of arrangements that may be employed to wear the incontinence pad 100 as described herein.

Beginning with step 703, the dental instrument 100 adapted to measure the degree of tapering of the side wall 206 of the tooth 200, as discussed herein, may be provided. For instance, the dental instrument 100 may include a handle 103 and a taper measuring component 106, where the taper measuring component 106 includes a bottom surface 124 formed at a coupling point of a second elongated member 118 and a third elongated member 121. The taper measuring component 106 may further include the second elongated member 118, the second elongated member 118 being configured to be substantially parallel to a vertical axis of the tooth 200 when the bottom surface 124 of the taper measuring component 106 is placed on the finishing line 218 of the tooth preparation. The taper measuring component 106 may further include the third elongated member 121, where the third elongated member 121 projects radially from the second elongated member 118 at a predefined angle (θ).

Next, in step 706, an operator may position the taper measuring component 106 of the dental instrument 100 adjacent to the tooth 200 or on the finishing line 218 of the tooth preparation using the handle 103. In some embodiments, the operator may position the bottom surface 124 of the taper measuring component 106 on the finishing line 218 of the prepared tooth (e.g., adjacent to the tooth 200).

In step 709, the operator may measure the degree of tapering of the side wall 206 of the tooth 200 based at least in part on whether the third elongated member 121 rests substantially flush along the side wall 206 of the tooth 200. For instance, if the third elongated member 121 does not rest substantially flush along the side wall 206 of the tooth 200, another instrument having a different predefined angle (θ) may be used, or a better eyeball test may be applied based on how closing the tapering of the side wall 206 of the tooth 200 conforms to the predefined angle (θ) of the taper measuring component 106. Alternatively, if the third elongated member 121 rests substantially flush along the side wall 206 of the tooth 200 and the second elongated member 118 substantially parallel to the vertical axis 212 (also referred to as the longitudinal axis) of the tooth 200, it may be assumed that the tapering of the side wall 206 of the tooth 200 is equal or substantially similar to the predefined angle (θ) of the taper measuring component 106.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A dental instrument for measuring a degree of tapering of a tooth, comprising:
   a handle; and
   a taper measuring component coupled to a distal end of the handle, the taper measuring component comprising:
      a first bend defining a first elongated member and a second elongated member, wherein the first elongated member extends from and is parallel to a body of the handle;
      a second bend defining the second elongated member and a third elongated member;
      a bottom surface defined by the second bend;
      wherein the second elongated member is configured to be substantially vertical when the bottom surface of the taper measuring component is placed adjacent to the tooth such that the second elongated member is substantially parallel to a vertical axis of a tooth; and
      wherein the third elongated member projects radially from the second elongated member at a predefined angle, the third elongated member being shaped and positioned to rest substantially flush along a side wall of the tooth in response to a degree of tapering of the tooth being substantially similar to the predefined angle.

2. The dental instrument of claim 1, wherein the taper measuring component is detachably attached to the handle.

3. The dental instrument of claim 1, wherein the predefined angle is one of: six degrees, eight degrees, twelve degrees, sixteen degrees, or seventeen degrees.

4. The dental instrument of claim 1, wherein the handle comprises an indicator indicative of the predefined angle at which the third elongated member projects radially from the second elongated member.

5. A dental instrument configured to be held by an operator to measure a degree of tapering of a tooth, wherein the dental instrument comprises:
   a handle; and
   a taper measuring component coupled to a distal end of the handle adapted to measure the degree of tapering of a side wall of the tooth, the taper measuring component comprising:
      a first elongated member extending from the handle;
      a second elongated member;

a third elongated member; and a bottom surface formed at a coupling point of the second elongated member and the third elongated member, wherein:

the second elongated member is configured to be substantially parallel to a vertical axis of the tooth when the bottom surface of the taper measuring component is placed adjacent to the tooth; and the third elongated member projects radially from the second elongated member at a predefined angle, the third elongated member being shaped and positioned to rest substantially flush along a surface of the side wall of the tooth in response to a degree of tapering of the tooth being substantially similar to the predefined angle.

6. The dental instrument of claim 5, wherein the second elongated members has a length between 12 mm and 15 mm and the third elongated member has a length between 12 mm and 15 mm.

7. The dental instrument of claim 5, wherein the predefined angle is one of: six degrees, eight degrees, twelve degrees, sixteen degrees, or seventeen degrees.

8. The dental instrument of claim 5, wherein the tooth is a model tooth or a mammalian tooth.

9. The dental instrument of claim 5, wherein the handle comprises an indicator indicative of the predefined angle.

10. The dental instrument of claim 9, wherein the indicator is color coded.

11. The dental instrument of claim 5, wherein at least one side of the third elongated member comprises a measuring component that provides a height of the tooth wall.

12. A method for measuring a degree of tapering of a tooth, comprising:

providing a dental instrument adapted to measure the degree of tapering of a side wall of the tooth, the dental instrument comprising:

a handle; and a taper measuring component comprising:

a first elongated member;

a bottom surface formed at a coupling point of a second elongated member and a third elongated member;

the second elongated member being configured to be substantially vertical when the bottom surface of the taper measuring component is placed adjacent to the tooth; and the third elongated member projecting radially from the first elongated member at a predefined angle;

positioning the taper measuring component on a finishing line of a tooth preparation; and measuring the degree of tapering of the side wall of the tooth based at least in part on whether the third elongated member rests substantially flush along the side wall of the tooth.

13. The method of claim 12, further comprising detaching or attaching the taper measuring component to the handle.

14. The method of claim 12, wherein the predefined angle is one of: six degrees, eight degrees, twelve degrees, sixteen degrees, or seventeen degrees.

15. The method of claim 12, wherein the handle comprises an indicator indicative of the predefined angle at which the third elongated member projects radially from the second elongated member.

16. The method of claim 12, wherein the second elongated members has a length between 12 mm and 15 mm and the third elongated member has a length between 12 mm and 15 mm.

17. The method of claim 12, wherein the tooth is a model tooth or a mammalian tooth.

\* \* \* \* \*